(12) United States Patent
Thiruvengadam et al.

(10) Patent No.: US 10,082,498 B2
(45) Date of Patent: Sep. 25, 2018

(54) METHODS FOR TREATING ADHD AND BIPOLAR DISORDER USING A MEMBRANE POTENTIAL RATIO TEST

(71) Applicant: PSYCHNOSTICS, LLC., Baltimore, MD (US)

(72) Inventors: Alagu P. Thiruvengadam, Baltimore, MD (US); Douglas B. Woodruff, Baltimore, MD (US)

(73) Assignee: PsychNostics, LLC, Baltimore, MD (US)

( * ) Notice: Subject to any disclaimer, the term of this patent is extended or adjusted under 35 U.S.C. 154(b) by 0 days.

(21) Appl. No.: 14/888,720

(22) PCT Filed: May 15, 2014

(86) PCT No.: PCT/US2014/038159
§ 371 (c)(1),
(2) Date: Nov. 3, 2015

(87) PCT Pub. No.: WO2014/186555
PCT Pub. Date: Nov. 20, 2014

(65) Prior Publication Data
US 2016/0084826 A1   Mar. 24, 2016

Related U.S. Application Data

(60) Provisional application No. 61/824,208, filed on May 16, 2013.

(51) Int. Cl.
*A61K 39/00* (2006.01)
*A61K 31/00* (2006.01)
*G01N 33/566* (2006.01)
*C12Q 1/00* (2006.01)
*G01N 33/50* (2006.01)
*G01N 33/68* (2006.01)

(52) U.S. Cl.
CPC ..... *G01N 33/5035* (2013.01); *G01N 33/6893* (2013.01); *G01N 2500/04* (2013.01); *G01N 2500/10* (2013.01); *G01N 2800/304* (2013.01); *G01N 2800/305* (2013.01)

(58) Field of Classification Search
None
See application file for complete search history.

(56) References Cited

U.S. PATENT DOCUMENTS

| | | | |
|---|---|---|---|
| 7,425,410 B2 * | 9/2008 | Thiruvengadam | G01N 33/5041 424/9.1 |
| 7,906,300 B2 * | 3/2011 | Thiruvengadam | C12Q 1/34 435/18 |
| 2007/0202486 A1 | 8/2007 | Umeda et al. | |
| 2008/0160554 A1 | 7/2008 | Thiruvengadam et al. | |

OTHER PUBLICATIONS

International Search Report of PCT/US2014/038159 dated Sep. 26, 2014 [PCT/ISA/210].

* cited by examiner

*Primary Examiner* — Olga N Chernyshev
(74) *Attorney, Agent, or Firm* — Sughrue Mion, PLLC

(57) ABSTRACT

The present invention relates to a method for optimizing drug therapy treatment of patients with Attention Deficit Hyperactivity Disorder (ADHD) or Bipolar Disorder (BD), a method of optimizing drug dosage for treatment of ADHD and BD, a method of treating ADHD and BD, and a kit. The present method may also be used to adjust medication doses for individual patients.

33 Claims, 6 Drawing Sheets

Figure 1: MPR™ Returns to ADHD Range After Cessation of Stimulants
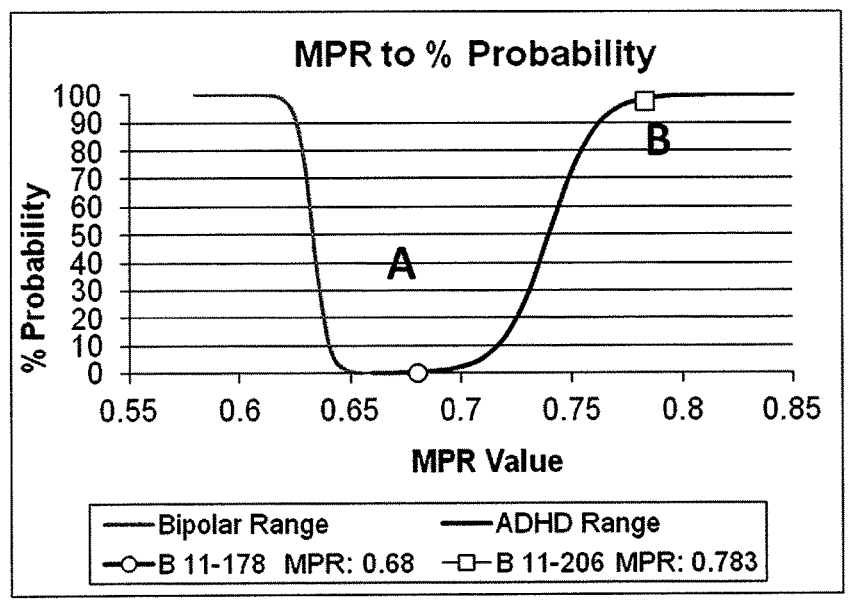

Figure 2: MPR™ Alerts to Comorbid ADHD and Returns to Negative Range After Treatment
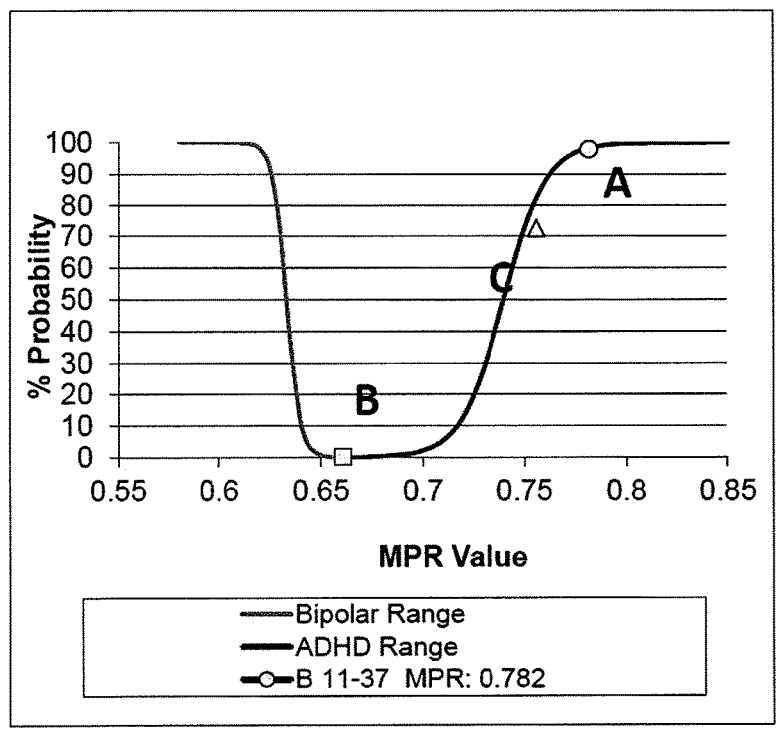

Figure 3: In BD Patient MPR™ Returns to Negative with Treatment
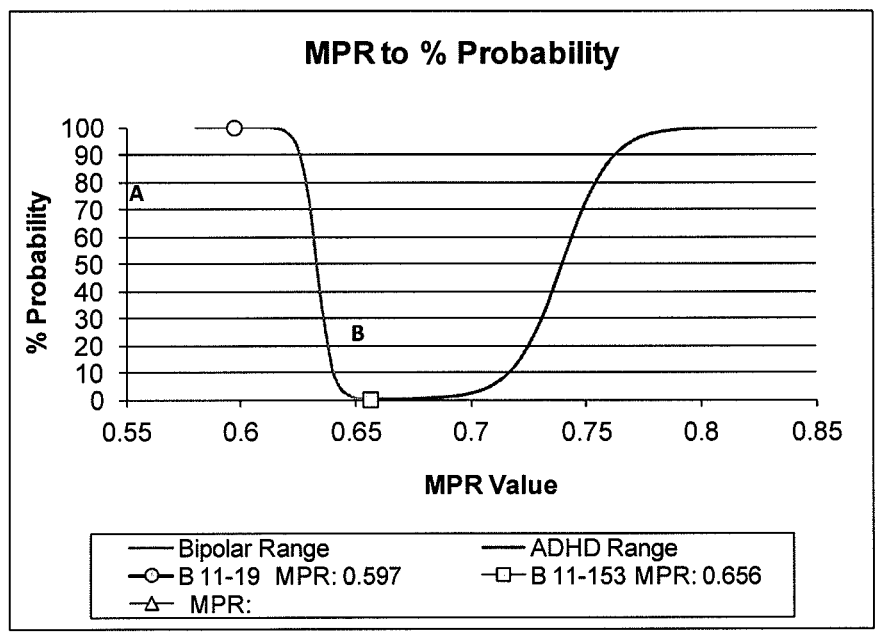

Figure 4: Example of BD Transition to ADHD
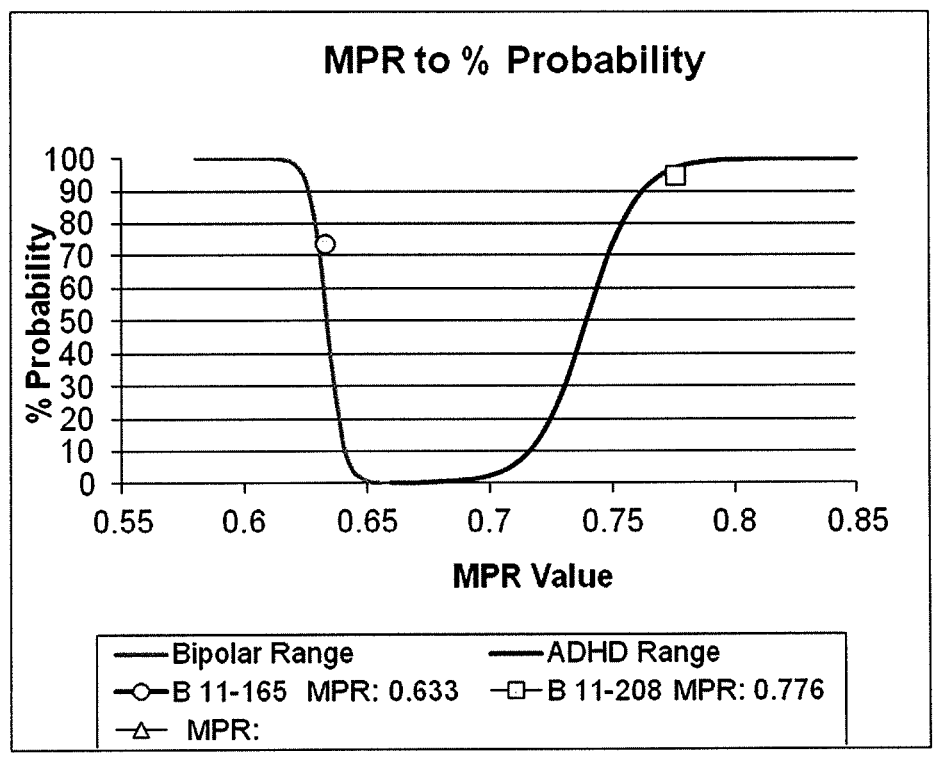

Figure 5: MPR™ Alerting to the Potential Presence of Comorbid ADHD
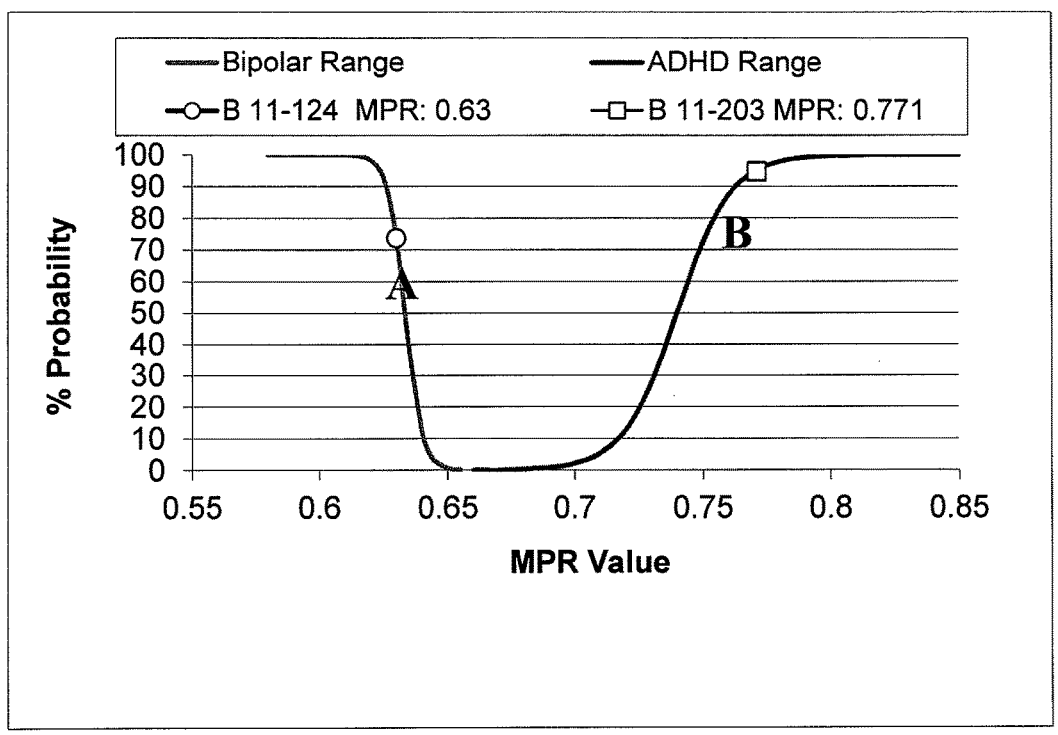

Figure 6: MPR™ Test Adjusted Overcorrection for ADHD Treatment
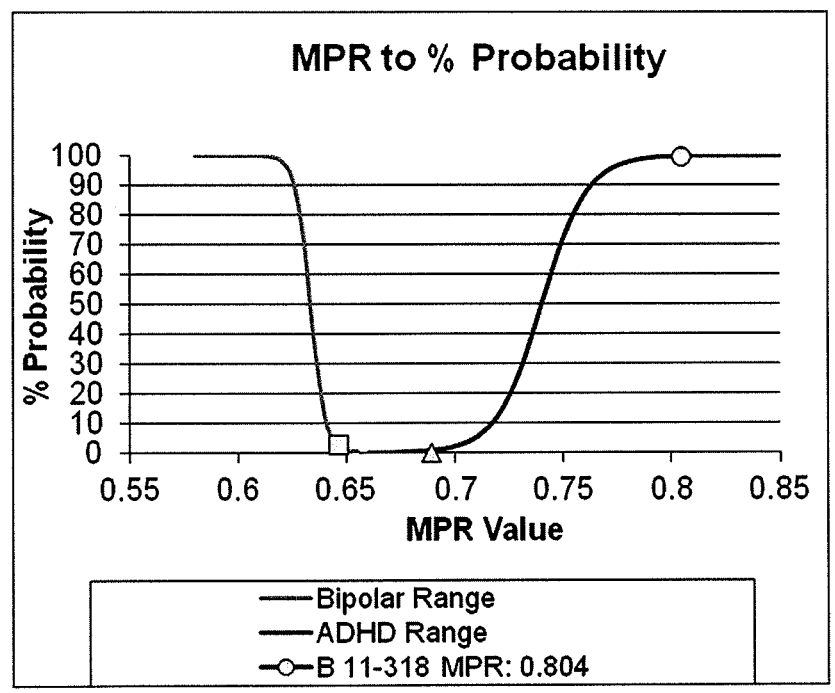

METHODS FOR TREATING ADHD AND BIPOLAR DISORDER USING A MEMBRANE POTENTIAL RATIO TEST

CROSS REFERENCE TO RELATED PATENT APPLICATION

This application is a National Stage of International Application No. PCT/US2014/038159, filed May 15, 2014, claiming the benefit of U.S. Provisional Application No. 61/824,208, filed May 16, 2013, which are incorporated herein by reference in their entirety.

FIELD OF THE INVENTION

The present invention is related to a method for optimizing drug therapy treatment for Attention Deficit Hyperactivity Disorder (ADHD) or Bipolar Disorder (BD), a method of optimizing drug dosage for treatment of ADHD and BD, and a method of treating ADHD and BD. Generally, this method involves determining changes that occur in the membrane potential in cells of individuals affected by ADHD or BD, as compared to cells of unaffected control individuals.

BACKGROUND OF THE INVENTION

Mental illness afflicts nearly ten percent of the general population both in the United States and in the rest of the world. Bipolar (manic depressive) disorder occurs in one to two percent of the population and is the sixth leading cause of disability (Coryell et al., *Am. J. Psychiatry* 150:720-727 (1993); Lopez, A. D., and Murray, C. C., *Nat. Med.* 4:1241-1243 (1998); Hyman, S. E., *Am. J. Geriatr. Psychiatry* 9:330-339 (2001)). A problem facing the medical community is misdiagnosis of bipolar disorder. Misdiagnosed patients receive an average of 3.5 misdiagnoses and consult four physicians before receiving an accurate diagnosis ("Living with bipolar disorder: How far have we really come?" National Depressive and Manic-Depressive Association, Chicago, Ill. (2001)).

Attention-deficit/hyperactivity disorder is characterized by persistent inattention and impulsivity. The criteria for this disorder are outlined, for example, in DSM-IV-TR (*Diagnostic and Statistical Manual of Mental Disorders*, Fourth Edition, *Text Revision* 2000, American Psychiatric Association, Washington D.C. (2000)). However misdiagnosis and over-diagnosis are common due to a number of barriers including limited access to available mental health services (National Institute of Health. Diagnosis and treatment of attention deficit hyper activity disorder. (1998); *NIH Consensus Statement*, 16(2):1-37 Foy J. M. and Earls, M. F., *Pediatrics* 115:97-104 (2005)).

The American Academy of Pediatricians has developed a community consensus for the diagnosis and management of ADHD. Still, there are large discrepancies between practice patterns and the guidelines. There is an urgent need for a simple blood test to identify this illness at an early stage and to treat patients adequately at an early point in time (Benazzi, F., Progress in *Neuro Psycopharmacology and Biological Psychiatry*, 29:267-274 (2005)).

The DSM-IV makes a distinction between bipolar I (BPI) and bipolar II (BPII) disorders. Moreover, the symptoms of ADHD are very similar to bipolar I and bipolar II symptoms. In order to better diagnose and treat patients, it can be important to distinguish between these three diseases. The current diagnostic method for bipolar disorders and ADHD involves a series of clinical interviews and examination using the DSM-IV-TR, the main diagnostic reference of Mental Health professionals in the United States, which is now in its fourth edition. Significant controversy exists about the validity of this manual, which limits the accuracy of clinical diagnosis (Torrey et al, "Surviving Manic Depression", Basic Books, New York (2002)). In addition, attempts are genes underlying this diagnostic markers. and possible use as underway to identify the illness and thereby develop. However, their identification diagnostic markers are years away (Bradbury, J., *Lancet* 357:1596 (2001)).

According to Benazzi (Benazzi F., Mixed depression: a critical marker of bipolar II disorder, *Progress in Neuro-Psycopharmacology and Biological Psychiatry*, 29:267-274 (2005)) under diagnosis and misdiagnosis of BPII are common in clinical practice. In a recent lecture entitled "Bipolar One and Bipolar Two: Will the Real Bipolar Disorder Please Stand Up?", DePaulo (Fifth Annual Course, Dept. Psychiatry and Behavioral Sciences, Johns Hopkins University, Nov. 6, 2004) highlights the importance of this problem in the diagnosis and treatment in a clinical setting.

The lifetime risk for unipolar disorder (major depressive disorder) is 10% to 25% for women and from 5% to 12% for men. At any point in time, 5% to 9% of women and 2% to 3% of men suffer from this disorder. Prevalence is unrelated to ethnicity, education, income, or marital status.

Like bipolar disorder, unipolar disorder is also currently diagnosed using the DSM-IV. By definition, unipolar disorder and bipolar disorder are distinct conditions. Unipolar disorder is diagnosed when there has never been a manic episode and at least five of the following symptoms have been present during the same 2 week depressed period:

Abnormal depressed mood.
Abnormal loss of all interest and pleasure.
Appetite or weight disturbance, either:
  Abnormal weight loss (when not dieting) or decrease in appetite.
  Abnormal weight gain or increase in appetite.
Sleep disturbance, either abnormal insomnia or abnormal hypersomnia.
Activity disturbance, either abnormal agitation or abnormal slowing (observable by others).
Abnormal fatigue or loss of energy.
Abnormal self-reproach or inappropriate guilt.
Abnormal poor concentration or indecisiveness.
Abnormal morbid thoughts of death or suicide.

There is evidence that unipolar disorder is, in part, a genetic disorder. Therefore, as with bipolar disorder, attempts are underway to identify the genes underlying unipolar disorder and thereby develop diagnostic markers. However, this has yet to be achieved.

In virtually every animal cell, the concentration of $Na^+$ in the cell (~12 mM) is lower than the concentration of $Na^+$ in the surrounding medium (~145 mM), and the concentration of $K^+$ in the cell (~140 mM) is higher than the concentration of $K^+$ in the surrounding medium (~4 mM). This imbalance is established and maintained by an active transport system in the plasma membrane. The transporter enzyme $Na^+K^+$ ATPase, also known as the sodium pump, couples breakdown of ATP to the simultaneous movement of both $Na^+$ and $K^+$ against their electrochemical gradients. For each molecule of ATP hydrolyzed to ADP and $P_i$, the $Na^+K^+$ ATPase transports two $K^+$ ions inward and three $Na^+$ ions outward across the plasma membrane.

The $Na^+K^+$ ATPase is an integral protein with two subunits ($M_r$~50,000 and ~110,000), both of which span the membrane. A proposed mechanism by which ATP hydrolysis is coupled to ion transport involves the Na$^+$K$^+$ ATPase cycling between two forms, a phosphorylated form with high affinity for K$^+$ and low affinity for Na$^+$, and a dephosphorylated form with high affinity for Na$^+$ and low affinity for K$^+$. The conversion of ATP to ADP and P$_i$ occurs in two steps catalyzed by the enzyme.

In addition to the Na$^+$K$^+$ ATPase, the plasma membrane also contains channel proteins that allow the principal cellular ions (Na$^+$, K$^+$, Ca$^{2+}$, and Cl$^-$) to move through them at different rates down their concentration gradients. Ion concentration gradients generated by pumps and selective movement of ions through channels constitutes the principal mechanism by which a difference in voltage, or electric potential, is generated across the plasma membrane. The permeability of K+ channels is nearly 100 times that of Na$^+$, Ca$^{2+}$, and Cl$^-$ channels. This the main reason the contribution from Na$^+$, Ca$^{2+}$, and Cl$^-$ channels to membrane potential is not significant. As a result, the major ionic movement across the plasma membrane is that of K$^+$ from the inside outward, powered by the K$^+$ concentration gradient, leaving an excess of negative charge on the inside and creating an excess of positive charge on the outside.

The magnitude of this membrane potential generally is −50 mV to −70 mV (with the inside of the cell negative relative to the outside), which is characteristic of most animal cells and essential to the conduction of action potentials in neurons. As noted earlier, the K$^+$ concentration gradient that drives the flow of K$^+$ ions through open K$^+$ channels is generated by the Na$^+$K$^+$ ATPase. The central role of the Na$^+$K$^+$ ATPase is reflected in the energy invested in this reaction: about 25% of the total energy consumption of a human at rest.

The steroid derivative ouabain is a potent and specific inhibitor of the Na$^+$K$^+$ ATPase. Ouabain and another steroid derivative, digitoxigenin, are the active ingredients of digitalis, which has long been used to treat congestive heart failure. Inhibition of the Na$^+$K$^+$ ATPase by digitalis leads to an increased Na$^+$ concentration in cells, activating a Na$^+$Ca$^{2+}$ antiporter in cardiac muscle. The increased influx of Ca$^{2+}$ through this antiporter produces elevated cytosolic Ca$^{2+}$, which strengthens the contractions of heart muscle.

The Na$^+$K$^+$ ATPase has also been investigated for its possible involvement in bipolar disorder pathophysiology (El-Mallakh et al, *Biol. Phychiatry*, 537:235-244 (1995)). However, this has been an unsettled and controversial subject in the field for many years. Na$^+$K$^+$ ATPase activity has been variously reported to be increased, decreased, or unchanged in bipolar patients. In 1997, Looney et al conducted a meta-analysis of the available literature on erythrocyte Na$^+$K$^+$ ATPase activity in bipolar disorder and concluded that it is lower in bipolar patients (Looney et al, *Depress. Anxiety*, 5:53-65 (1997)). However, the question of exactly how the Na$^+$K$^+$ ATPase plays a role in bipolar disorder remains unanswered.

Lithium, an alkaline metal that has been used successfully for over fifty years to stabilize mood in bipolar disorder, has been shown to augment Na$^+$K$^+$ ATPase activity. Recently, the role of lithium in depolarizing the resting membrane potential of neurons has been analyzed (Thiruvengadam, *J. Affect. Disord.*, 65:95-99 (2001); and Thiruvengadam, "Electro-biochemical coupling, excitability of neurons and bipolar disorder, *Bipolar Disorder* 3 (2001)). Hyperpolarization of membrane potential in leukocytes of bipolar patients and depolarization following the addition of lithium has been observed (El Mallakh et al, *J. Affect. Disord.*, 41:33-37 (1996)). In addition, a significantly smaller increase in Na$^+$K$^+$ ATPase density after incubation for 72 hours in ethacrynate or lithium has been observed in cells of bipolar patients compared to cells of unaffected individuals (Wood et al, *J. Affect. Disord.*, 21:199-206 (1991)).

El-Mallakh et al measured the transmembrane potential in leukocytes from hospitalized bipolar patients and observed that the transmembrane potential of the bipolar patients was hyperpolarized compared with normal controls and euthymic patients on lithium (El-Mallakh et al, *J. Affect. Disord.*, 41:33-37 (1996)). However, Tamella et al measured the membrane potentials of cultured lymphoblasts and concluded that there was no significant difference in membrane potentials among bipolar patients, their siblings and normal controls (Tamella et al, *Psychiatry Res.* 59:197-201 (1996)).

In view of the previous studies on the possible involvement of the Na$^+$K$^+$ ATPase in bipolar disorder, one would not expect Na$^+$K$^+$ ATPase activity to serve as a reliable basis for diagnosing bipolar disorder in an individual patient, because measurements of Na$^+$K$^+$ ATPase activity are highly variable. Similarly, one would not expect transmembrane potential to serve as a reliable basis for diagnosing bipolar disorder in an individual patient, because measurements of transmembrane potential are highly variable.

Accordingly, despite the existence of treatments for bipolar disorder and ADHD and recent advances in the psychiatric field, there remains a heretofore unmet need for clinical tests to augment the DSM-IV in diagnosing bipolar disorder and ADHD.

The present invention is directed to overcoming these and other deficiencies in the art.

SUMMARY OF THE INVENTION

The present invention relates to the fields of clinical psychiatry, clinical psychology and more specifically to the treatment of patients with BD and ADHD using a membrane potential ratio (MPR™) Test following diagnosis of a patient with BD or ADHD. One aspect of the present invention allows for the determination of an optimal effective therapy for treatment of patients diagnosed with ADHD or BD.

Currently there is no objective method to measure the response of BD and ADHD patients to available treatments and to determine the effectiveness of a given treatment independently for each treatment after the diagnosis has been made using the MPR™ test. Clinicians can use the MPR™ value for successfully treating the patients.

The MPR™ test has been described in U.S. Pat. Nos. 7,425,410 and 7,906,300, as well as U.S. Provisional Application Nos. 61/543,061 and 61/653,579, which are hereby incorporated by reference in their entirety.

The MPR™ test is used to diagnose BD and ADHD. Briefly, the MPR™ test involves measuring the membrane potential of the human cells in a test buffer and in a reference buffer and calculating the ratio of these membrane potentials. U.S. Pat. Nos. 7,425,410 and 7,906,300 describe the use of this method to diagnose both BD and ADHD. The present inventors have discovered that this method can be used to optimize treatment of patients with appropriate medications by measuring and/or adjusting the MPR™ values. For example, if the patients respond to the treatment then the MPR™ values return to negative range. Otherwise the treatment protocol is adjusted appropriately till the MPR™ value reaches the negative range.

Briefly, the membrane potentials of whole blood cells are measured using two different buffers in a plate reader. The mean MPR™ value is the ratio between the membrane potential of a patient's cells in the test buffer as the numerator and that in the reference buffer as the denominator determined by statistical analysis of multiple measurements, using the ANOVA and the multiple statistical regression analysis. See Thiruvengadam et al., *J Affect Disord* 100(1-3):75-82 (2007), which is hereby incorporated by reference in its entirety.

MPR™ is also useful in monitoring patient compliance. Recent prescribing information bulletin on Methylphenidate (trade name Ritalin) by the manufacturer Novartis Pharmaceuticals Corporation recommends that the dosage should be individualized according to the needs and responses of the patients. The recommended starting dose of Ritalin LA is 20 mg once daily. Dosage may be adjusted in weekly 10 mg increments to a maximum of 60 mg/day taken once daily in the morning, depending on tolerability and degree of efficacy observed. Daily dosage above 60 mg is not recommended. Heart disease, euphoria, abuse and addiction are major side effects of improper dosage. When, in the judgment of the clinician, a lower initial dose is appropriate, patients may begin treatment with 10 mg. However, in some patients even 10 mg may be too much. (See e.g., "Drug Facts: Stimulant ADHD Medications—Methylphenidate and Amphetamines" at drugabuse.gov/publications/drug-facts/stimulant-adhd-medications-methylphenidate-amphet-amines, which is hereby incorporated by reference in its entirety). There is no objective method of determining whether the prescribed dosage is appropriate. Moreover, there is no empirical evidence of greater improvement with higher doses of stimulants and any beneficial effect is likely to be compromised by the adverse effects, some of which can be very serious (Sachdev et al., *N Z J Psychiatry*, August; 34(4):645-50 (2000), which is hereby incorporated by reference in its entirety).

Lithium salts, once the mainstay of therapy for bipolar disorder, have tolerability issues at a higher dosage that often limit adherence (Nierenberg et al., *Am J Psychiatry*, January 1; 170(1):102-10 (2013), which is hereby incorporated by reference in its entirety). These findings highlight the persistent and chronic nature of bipolar disorder as well as the magnitude of unmet needs in its treatment. Moreover, the following side effects are common on lithium (helpguide.org/mental/bipolar_disorder_medications.htm). For example, weight gain, drowsiness, tremors, weakness or fatigue, excessive thirst; increased urination, stomach pain, thyroid problems, memory and concentration problems, nausea, vertigo, and diarrhea. Some of these side effects may go away as the subject's body adapts to the medication.

Clinicians can use MPR™ for screening and diagnosis of BD and ADHD. It takes seven years and four psychiatrists before a patient with Bipolar Disorder is correctly diagnosed. About 80 percent of antidepressants are prescribed by medical professionals other than psychiatrists. Only about one in ten adults who have ADHD/ADD are currently diagnosed and treated.

Also, clinicians can use the MPR™ for successfully treating the patients and adapting the treatment plan for each individual patient. A patient cannot fake a biomarker, but symptoms can be over reported or under reported by a patient (seeking stimulants, for instance). It is believed that this biomarker can help to undermine stigma. The methods according to the present invention can be used to prevent stimulant abuse.

The methods according to the present invention can be used to verify patient response to prescribed stimulant. This method can also be used to treat the patients with appropriate medications by measuring the MPR™ values. For example, if the patients respond to the treatment then the MPR™ values return to negative range. Otherwise the treatment protocol is adjusted appropriately till the MPR™ value reaches the negative range.

The methods according to the present invention may be used to adjust dosage of stimulants or drugs/medications. For example, when in the judgment of the clinician a lower initial dose is appropriate, patients may begin treatment with 10 mg in some patients even 10 mg may be too much as described in the examples cited below.

The methods according to the present invention may be used to diagnose both BD and ADHD. Moreover, the methods according to the present invention may be used to optimize treatment based on an earlier clinical diagnosis.

The following references are hereby incorporated by reference in their entirety:

Thiruvengadam et al., *J Affect Disord* 100(1-3):75-82 (2007).

Woodruff et al., *ADHD Atten Def Hyp Disord* September; 3(3):265-9 (2011).

Woodruff et al., *Ann Clin Psychiatry* May; 24(2): 135-9 (2012).

"Stimulant dosing in adults with ADHD lower than effective levels" at verusmed.com/articles/view/50506.

Olfson, M. et al., Stimulant dosing for children with ADHD: a medical claims analysis, J. Am. Acad. Child. Adolesc. Psychiatry, 48(1): 51-9 (January 2009).

"Other anticonvulsant medications for bipolar disorder" at mentalhealth.about.com/od/psychopharmacology/a/bpdmeds_2.htm.

Compton, K. et al., "Distinguishing ADHD from juvenile bipolar disorder: A guide for primary care Pas," JAAPA, 19(12): 41-48 (December 2006).

Insel, T., "Transforming Diagnosis," at nimh.nih.gov/about/director/2013/transforming-diagnosis.shtml (Apr. 29, 2013).

Kapur, S. et al., "Why has it taken so long for biological psychiatry to develop clinical tests and what to do about it?" Mol. Psychiatry, 17(12): 1174-9 (December 2012).

Ritalin LA® label (Novartis), American Psychiatric Association, Diagnosis and Statistical Manual of Mental Disorders, $4^{th}$ Ed. (1994).

Medication Guide, Ritalin LA®, June 2012.

BRIEF DESCRIPTION OF THE DRAWINGS

All the figures show a plot of the mean MPR™ versus the % probability of the disorder as determined by the multiple statistical regressions. The data points for the specific drug treatment are superimposed on the solid line curves to indicate the patient's response to drug treatment. The blue portion of the solid line curve represents the BD range whereas the red portion represents the ADHD range.

FIG. 1 illustrates that for this patient, the MPR™ fairly quickly returns to the ADHD range from the negative range after stopping of relevant treatment, concordant with an increase in symptomatology.

FIG. 2 shows treatment of patients with comorbidity using the MPR™ Test.

FIG. 3 illustrates treatment of a bipolar patient. The result in the negative range helped in the decision to essentially stay the course with the medications associated with that result.

FIG. 4 showing example of a patient with bipolar symptoms in the transition region. After these symptoms were treated the patient still had ADHD symptoms which were successfully treated with help of the MPR™ test.

FIG. 5 showing detection for potential presence of comorbid ADHD or ADD.

FIG. 6 showing use of MPR™ test to adjust or titrate dosage of medication for optimum efficacy avoiding over dosage and under dosage.

DETAILED DESCRIPTION OF THE INVENTION

The present invention involves a method of optimizing drug therapy treatment for a human patient with attention-deficit/hyperactivity disorder (ADHD). The method includes obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$. The method also includes following treatment of the human patient with a drug therapy for ADHD comparing the ratio to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and wherein (b) is an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$. According to the present method, each mean membrane potential is determined by incubating the cells in vitro in buffer comprising a potential-sensitive dye, resuspending the cells in potential-sensitive dye free-buffer, and measuring cell fluorescence; and identifying an optimal drug therapy for treatment the human patient with ADHD when the ratio obtained is not significantly different from the control ratio in (a) and/or is significantly higher than the ADHD control ratio in (b).

A second aspect of the present invention is related to a method of determining an optimal drug treatment therapy for a human patient with bipolar disorder (BD). The method includes obtaining a ratio of a mean membrane potential from a first population of cells from the human patient incubated in vitro in the presence of a compound that alters Na+K+ ATPase activity and in the absence of K+, to a mean membrane potential from a second population of cells from the human patient incubated in vitro in the absence of the compound that alters Na+K+ ATPase activity and in the presence or absence of K+. The method also includes monitoring the treatment of a human patient with BD by determining the ratio to (a) and/or (b) and optimizing treatment, wherein (a) is a control ratio of a mean membrane potential of control human cells known to not have ADHD incubated in vitro in the presence of the compound that alters Na+K+ ATPase activity and in the absence of K+, to a mean membrane potential of the control human cells incubated in vitro in the absence of the compound that alters Na+K+ ATPase activity and in the presence or absence of K+, and wherein (b) is a BD control ratio of a mean membrane potential of ADHD control human cells known to have ADHD incubated in vitro in the presence of the compound that alters Na+K+ ATPase activity and in the absence of K+, to a mean membrane potential of the ADHD control human cells incubated in vitro in the presence of the compound that alters Na+K+ ATPase activity and in the presence or absence of K+. According to the method each mean membrane potential is determined by incubating the cells in vitro in buffer comprising a potential-sensitive dye, resuspending the cells in potential-sensitive dye free-buffer, and measuring cell fluorescence; and identifying an optimal drug therapy for treatment of the human patient with BD when the ratio obtained is not significantly different from the control ratio in (a) and/or is significantly lower than the BD control ratio in (b).

A third aspect of the present invention includes a method of optimizing a drug therapy treatment for a human patient with attention-deficit/hyperactivity disorder (ADHD), comprising the steps of:
1) performing a drug therapy treatment for the patient with ADHD with at least one drug;
2) obtaining at least one sample from the patient with ADHD which is collected after the drug therapy treatment with at least one drug;
3) performing on each sample, a mean membrane potential test including obtaining a ratio of a mean membrane potential from a first population of cells from the sample incubated in vitro in the presence of a compound that alters $Na^+K^+$ ATPase activity and in the absence of $K^+$, to a mean membrane potential from a second population of cells from the sample incubated in vitro in the absence of the compound that alters $Na^+K^+$ ATPase activity and in the presence or absence of $K^+$;
4) comparing the ratio of the mean membrane potential to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and (b) is an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$;
5) modifying at least one drug in the drug therapy treatment based on the mean membrane potential test; and
6) identifying an optimal drug therapy treatment for the human patient with ADHD when the ratio of the mean membrane potential obtained is not significantly different from the control ratio in (a) and/or is significantly higher than the ADHD control ratio in (b).

A fourth aspect of the invention includes a method of optimizing a drug therapy treatment for a human patient with bipolar disorder (BD), comprising the steps of:
1) performing a drug therapy treatment for the patient with BD with at least one drug;
2) obtaining at least one sample from the patient with BD which is collected after the drug therapy treatment with at least one drug;
3) performing on each sample, a mean membrane potential test including obtaining a ratio of a mean membrane potential from a first population of cells from the sample incubated in vitro in the presence of a compound that alters $Na^+K^+$ ATPase activity and in the absence of $K^+$, to a mean membrane potential from a second population of cells from the sample incubated in vitro in the absence of the compound that alters $Na^+K^+$ ATPase activity and in the presence or absence of $K^+$;

4) comparing the ratio of the mean membrane potential to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and (b) is a BD control ratio of a mean membrane potential of BD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$;

5) modifying at least one drug in the drug therapy treatment based on the mean membrane potential test; and 6) identifying an optimal drug therapy treatment for the human patient with BD when the ratio of the mean membrane potential obtained is not significantly different from the control ratio in (a) and/or is significantly lower than the BD control ratio in (b).

A fifth aspect of the invention includes a method of optimizing a drug dosage for treatment of a human patient with attention-deficit/hyperactivity disorder (ADHD), including obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug dosage for ADHD and comparing the ratio to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and wherein (b) is an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$. According to the method each mean membrane potential is determined by incubating the cells in vitro in buffer comprising a potential-sensitive dye, resuspending the cells in potential-sensitive dye free-buffer, and measuring cell fluorescence. The method also includes identifying an optimal drug dosage for treatment of the human patient with ADHD when the ratio obtained is not significantly different from the control ratio in (a) and/or is significantly higher than the ADHD control ratio in (b).

A sixth aspect of the invention involves a method of optimizing a drug dosage for treatment of a human patient with bipolar disorder (BD), including obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug dosage for ADHD; and comparing the ratio to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$ and wherein (b) is a BD control ratio of a mean membrane potential of BD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$. According to the method each mean membrane potential is determined by incubating the cells in vitro in buffer comprising a potential-sensitive dye, resuspending the cells in potential-sensitive dye free-buffer, and measuring cell fluorescence. The method also includes identifying an optimal drug dosage for treatment of the human patient with BD when the ratio obtained is not significantly different from the control ratio in (a) and/or is significantly lower than the BD control ratio in (b).

A seventh aspect of the invention includes a method of optimizing a drug dosage for treatment of a human patient with attention-deficit/hyperactivity disorder (ADHD). The method includes the steps of:

1) treating the human patient with a dosage of a drug for ADHD;

2) obtaining at least one sample from the human patient which is collected after the treating step;

3) performing on each sample, a mean membrane potential test including obtaining a ratio of a mean membrane potential from a first population of cells from the sample incubated in vitro in the presence of a compound that alters $Na^+K^+$ ATPase activity and in the absence of $K^+$, to a mean membrane potential from a second population of cells from the sample incubated in vitro in the absence of the compound that alters $Na^+K^+$ ATPase activity and in the presence or absence of $K^+$;

4) comparing the ratio of the mean membrane potential to (a) and/or (b) wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and (b) is an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters Na+K+ ATPase activity and in the presence or absence of K+;
5) modifying the drug dosage based on the mean membrane potential test; and
6) identifying an optimal drug dosage for treating the human patient when the ratio of the mean membrane potential obtained is not significantly different from the control ratio in (a) and/or is significantly higher than the ADHD control ratio in (b).

An eighth aspect of the invention is related to a method of optimizing a drug dosage for treatment of a human patient bipolar disorder (BD). The method includes the steps of:
1) treating the human patient with a dosage of a drug for BD;
2) obtaining at least one sample from the human patient which is collected after the treating step;
3) performing on each sample, a mean membrane potential test including obtaining a ratio of a mean membrane potential from a first population of cells from the sample incubated in vitro in the presence of a compound that alters Na+K+ ATPase activity and in the absence of K+, to a mean membrane potential from a second population of cells from the sample incubated in vitro in the absence of the compound that alters Na+K+ ATPase activity and in the presence or absence of K+,
4) comparing the ratio of the mean membrane potential to (a) and/or (b) wherein (a) is a control ratio of a mean membrane potential of control human cells known to not have ADHD incubated in vitro in the presence of the compound that alters Na+K+ ATPase activity and in the absence of K+, to a mean membrane potential of the control human cells incubated in vitro in the absence of the compound that alters Na+K+ ATPase activity and in the presence or absence of K+, and (b) is a BD control ratio of a mean membrane potential of BD control human cells known to have BD incubated in vitro in the presence of the compound that alters Na+K+ ATPase activity and in the absence of K+, to a mean membrane potential of the BD control human cells incubated in vitro in the presence of the compound that alters Na+K+ ATPase activity and in the presence or absence of K+;
5) modifying the drug dosage based on the mean membrane potential test; and
6) identifying an optimal drug dosage for treating the human patient when the ratio of the mean membrane potential obtained is not significantly different from the control ratio in (a) and/or is significantly lower than the BD control ratio in (b).

A ninth aspect of the invention is related to a method of treating a human patient with attention-deficit/hyperactivity disorder (ADHD). The method includes obtaining a ratio of a mean membrane potential from a first population of cells from the human patient incubated in vitro in the presence of a compound that alters Na+K+ ATPase activity and in the absence of K+, to a mean membrane potential from a second population of cells from the human patient incubated in vitro in the absence of the compound that alters Na+K+ ATPase activity and in the presence or absence of K+, following treatment of the human patient with a drug dosage for ADHD. The method also includes comparing the ratio to (a) and/or (b) wherein (a) is a control ratio of a mean membrane potential of control human cells known to not have ADHD incubated in vitro in the presence of the compound that alters Na+K+ ATPase activity and in the absence of K+, to a mean membrane potential of the control human cells incubated in vitro in the absence of the compound that alters Na+K+ ATPase activity and in the presence or absence of K+, and (b) is an ADHD control ratio of a mean membrane potential of ADHD control human cells known to have ADHD incubated in vitro in the presence of the compound that alters Na+K+ ATPase activity and in the absence of K+, to a mean membrane potential of the ADHD control human cells incubated in vitro in the presence of the compound that alters Na+K+ ATPase activity and in the presence or absence of K+. According to the method, each mean membrane potential is determined by incubating the cells in vitro in buffer comprising a potential-sensitive dye, resuspending the cells in potential-sensitive dye free-buffer, and measuring cell fluorescence; and adjusting the drug dosage for treating the human patient such that the ratio obtained is not significantly different from the control ratio in (a) and/or is significantly higher than the ADHD control ratio in (b).

A tenth aspect of the invention includes a method of treating a human patient with bipolar disorder (BD). The method includes obtaining a ratio of a mean membrane potential from a first population of cells from the human patient incubated in vitro in the presence of a compound that alters Na+K+ ATPase activity and in the absence of K+, to a mean membrane potential from a second population of cells from the human patient incubated in vitro in the absence of the compound that alters Na+K+ ATPase activity and in the presence or absence of K+, following treatment of the human patient with a drug dosage for ADHD; comparing the ratio to (a) and/or (b) wherein (a) is a control ratio of a mean membrane potential of control human cells known to not have BD incubated in vitro in the presence of the compound that alters Na+K+ ATPase activity and in the absence of K+, to a mean membrane potential of the control human cells incubated in vitro in the absence of the compound that alters Na+K+ ATPase activity and in the presence or absence of K+, and wherein (b) is a BD control ratio of a mean membrane potential of BD control human cells known to have BD incubated in vitro in the presence of the compound that alters Na+K+ ATPase activity and in the absence of K+, to a mean membrane potential of the BD control human cells incubated in vitro in the presence of the compound that alters Na+K+ ATPase activity and in the presence or absence of K+. According to the method each mean membrane potential is determined by incubating the cells in vitro in buffer comprising a potential-sensitive dye, resuspending the cells in potential-sensitive dye free-buffer, and measuring cell fluorescence; and adjusting drug dosage for treating the human patient such that the ratio obtained is not significantly different from the control ratio in (a) and/or is significantly lower than the BD control ratio in (b).

An eleventh aspect of the invention is related to a method of treating a human patient with attention-deficit/hyperactivity disorder (ADHD). The method includes the steps of:
1) treating the human patient with a dosage of a drug for ADHD;
2) obtaining at least one sample from the human patient which is collected after the treating step;
3) performing on each sample, a mean membrane potential test including obtaining a ratio of a mean membrane potential from a first population of cells from the sample incubated in vitro in the presence of a compound that alters Na+K+ ATPase activity and in the absence of K+, to a mean membrane potential from a second population of cells from the sample incubated in vitro in the absence of the compound that alters Na+K+ ATPase activity and in the presence or absence of K+;
4) comparing the ratio of the mean membrane potential to (a) and/or (b), wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and (b) is an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$;

5) adjusting the drug dosage for treating the human patient such that ratio of the mean membrane potential obtained is not significantly different from the control ratio in (a) and/or is significantly higher than the ADHD control ratio in (b).

A twelfth aspect of the invention is related to a method of treating a human patient with bipolar disorder (BD). The method includes the steps of:

1) treating the human patient with a dosage of a drug for BD;
2) obtaining at least one sample from the human patient which is collected after the treating step;
3) performing on each cell sample, a mean membrane potential test including obtaining a ratio of a mean membrane potential from a first population of cells from the cell sample incubated in vitro in the presence of a compound that alters $Na^+K^+$ ATPase activity and in the absence of $K^+$, to a mean membrane potential from a second population of cells from the cell sample incubated in vitro in the absence of the compound that alters $Na^+K^+$ATPase activity and in the presence or absence of $K^+$;
4) comparing the ratio of the mean membrane potential to (a) and/or (b), wherein (a) is a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, and wherein (b) is a BD control ratio of a mean membrane potential of ADHD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$;
5) adjusting the drug dosage for treating the human patient such that ratio of the mean membrane potential obtained is not significantly different from the control ratio in (a) and/or is significantly lower than the BD control ratio in (b).

A thirteenth aspect of the present invention is related to a kit. The kit includes a reference buffer and a test buffer with a potential-sensitive dye. The reference buffer is a $K^+$-containing buffer such as, but not limited to, a HEPES buffer. The test buffer is a $K^+$-free buffer such as, but not limited to, a $K^+$-free HEPES buffer. Preferably, the pH range of the reference and test buffers is in the range of 6.6 to 7.5.

In a preferred embodiment, the kit includes a) a $K^+$-containing HEPES reference buffer having a pH range of 7.3 to 7.5; b) a $K^+$-free HEPES test buffer having a pH range of 6.6 to 7.0; c) a potential-sensitive dye; and d) a compound that alters $Na^+K^+$ ATPase activity.

In some embodiments, the methods according to first to twelfth aspect of the present invention further include obtaining an initial ratio of a mean membrane potential from an initial population of cells from the human patient before the obtaining step or the treating step.

In another embodiment, the methods according to any one of first to twelfth aspects of the present invention include performing steps to obtain (a) and (b).

A cell's membrane potential is the result of the different concentration of ions on either side of the membrane. The activity of the $Na^+K^+$ ATPase pump, which regulates the concentration of $Na^+$ and $K^+$ to maintain homeostasis, can be altered by a variety of external stimuli, including various chemicals. When the $Na^+$ and $K^+$ ionic gradients are modulated by some means, the cell regulates the activity of the $Na^+K^+$ ATPase in an effort to return the ionic gradients to normal levels. Some compounds, such as ethacrynate, monensin, and monensin decyl ester, alter the activity of the $Na^+K^+$ ATPase by increasing the intracellular levels of sodium. Other modulators of $Na^+K^+$ ATPase include, but are not limited to, phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate. Other phorbol esters alter the activity of the $Na^+K^+$ ATPase by increasing the density of the $Na^+K^+$ ATPase on the cell surface. Thus, the activity of the $Na^+K^+$ ATPase is affected by its structure, its density, and compounds (both endogenous and exogenous) that affect the structure and density.

Table 1 below shows other examples of compounds that alter the activity of the $Na^+K^+$ ATPase, either indirectly by altering the $K^+$ and/or $Na^+$ ionic gradients or by acting on the $Na^+K^+$ ATPase itself.

TABLE 1

| Chemical | $K^+$ | $Na^+$ | $K^+$ & $Na^+$ | $Na^+K^+$ ATPase |
|---|---|---|---|---|
| Valinomycin | X | | | |
| Monensin | | X | | |
| Gramicidin | | X | | |
| PCMBS | | X | | |
| Veratridine | | X | | |
| Ethacrynate | | | X | |
| PMA | | | | X |
| Dopamine | | | | X |
| Catacholamines | | | | X |
| Phorbol Esters | | | | X |
| Ouabain | | | | X |
| Lithium | X | X | X | X |
| Valproate | | | | X |
| Lamotrigine | | | | X |
| Cocaine | | | X | |
| Nicotine | | X | | |
| RO-31-8220 | | | | X |
| Oxymetazoline | | | | X |
| Calcineurin | | | | X |
| Topiramate | | | | X |
| Peptide Hormones | | | | X |
| Sorbitol | | | | X |
| Diuretics | | | X | |

The compounds that are described herein are merely examples of the compounds that could be used to alter $Na^+K^+$ ATPase activity. For example, any compound that increases the density and/or activity of the Na$^+$K$^+$ ATPase can be used in the methods according to the present invention.

The phorbol ester according to the present invention include phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate.

The present methods employ Na$^+$K$^+$ ATPase-altering compounds to determine drug treatment therapy for patients with a bipolar disorder, as well as optimization of the same. In other embodiments, the methods according to the present invention employ such Na$^+$K$^+$ ATPase-altering compounds to determine drug treatment therapy for patients with ADHD, as well as optimization of the same.

In another embodiment, a compound that decreases the density and/or activity of the Na$^+$K$^+$ ATPase may be used in a method according to the present invention. For example, low concentrations of ouabain may be useful in differentiating bipolar cells from normal cells.

Thus, for purposes of this disclosure, "alters Na$^+$K$^+$ ATPase activity" includes directly altering Na$^+$K$^+$ ATPase activity by acting directly upon the Na$^+$K$^+$ ATPase as well as indirectly altering Na$^+$K$^+$ ATPase activity by, for example, increasing the intracellular sodium concentration. Furthermore, "alters Na$^+$K+ ATPase activity" includes increasing or decreasing Na$^+$K$^+$ ATPase activity, although increasing Na$^+$K$^+$ ATPase activity is preferred.

Potassium uptake in cells of bipolar patients is significantly reduced compared to potassium uptake in cells of normal, unaffected patients. In several embodiments of the present invention, the membrane potential of cells incubated in potassium-free buffer is ascertained with or without incubation with compounds that alter the activity of the Na$^+$K$^+$ ATPase.

Examples of buffers that may be used in the methods according to the present invention, along with their useful pH ranges, are shown in Table 2 below.

TABLE 2

| Composition | Lower pH | Upper pH |
| --- | --- | --- |
| Glycyl-glycine-piperazine-2HCl—NaOH | 4.4 | 10.8 |
| MES-NaOH—NaCl | 5.2 | 7.1 |
| TRIS-malic acid-NaOH | 5.2 | 8.6 |
| MES-NaOH | 5.6 | 6.8 |
| ADA-NaOH—NaCl | 5.6 | 7.5 |
| ACES-NaOH—NaCl | 5.9 | 7.8 |
| ACES-NaOH—NaCl | 5.9 | 7.8 |
| BES-NaOH—NaCl | 6.2 | 8.1 |
| MOPS-NaOH—NaCl | 6.25 | 8.15 |
| TES-NaOH—NaCl | 6.55 | 8.45 |
| MOPS-KOH | 6.6 | 7.8 |
| HEPES-NaOH—NaCl | 6.6 | 8.5 |
| TRIS-HCl | 7.0 | 9.0 |
| HEPPSO-NaOH | 7.4 | 8.4 |
| BICINE-NaOH—NaCl | 7.4 | 9.3 |
| TAPS-NaOH—NaCl | 7.45 | 9.35 |
| HEPPS (EPPS)-NaOH | 7.5 | 8.7 |
| TRICINE-NaOH | 7.6 | 8.6 |
| BICINE-NaOH | 7.7 | 8.9 |

Potassium-containing buffers that may be used in the methods according to the present invention can be created by adding potassium to the buffers shown in the table above that do not contain potassium. Potassium-containing buffers useful in the methods according to the present invention preferably have a K$^+$ concentration in the range of approximately 2 mM to 7 mM, more preferably have a K$^+$ concentration of approximately 5 mM, and still more preferably have a K$^+$ concentration of 5 mM.

The K$^+$-containing buffer used in the examples set forth below is a HEPES buffer to which potassium has also been added (5 mM KCl, 4 mM NaHCO$_3$, 5 mM HEPES, 134 mM NaCl, 2.3 mM CaCl$_2$, and 5 mM glucose; pH 7.3-7.5, preferably 7.4), and is also referred to as "regular" or "stock" or "reference" buffer. The K$^+$-free buffer used in the examples is a HEPES buffer without potassium (4 mM NaHCO$_3$, 5 mM HEPES, 134 mM NaCl, 2.3 mM CaCl$_2$, and 5 mM glucose; pH 6.6-7.0, preferably 6.8), and is also referred to as "test" buffer.

The membrane potential of a patient's cells may be ascertained by any conventional method, such as by examining the fluorescence intensity of a potential-sensitive lipophilic fluorescent dye. The membrane potential is directly proportional to the intensity of fluorescence according to the following equation: I=CV, wherein I is the fluorescence intensity of a lipophilic fluorescent dye, V is the voltage or membrane potential, and C is a constant that can vary depending on a number of factors such as, but not limited to, temperature, lamp intensity, number of cells, concentration of the fluorescent dye, incubation time, and lipid composition of cells used. The calibration and determination of the value for C can be a cumbersome and unreliable procedure. Thus, according to the present invention, by using the ratio of the fluorescence intensity ($I_1$) of one sample of cells to the fluorescence intensity ($I_2$) of another sample of cells, the constant (C) is canceled out. Such ratio-metric measurements are preferred over absolute measurements.

Examples of potential-sensitive dyes that may be adapted for use in the present invention, along with their charges and optical responses, are shown below in Table 3 (all available from Molecular Probes Inc., Eugene, Oreg., US).

TABLE 3

| Dye | Structure (Charge) | Optical Response |
| --- | --- | --- |
| DiOC$_2$(3) | Carbocyanine | Slow; fluorescence response to |
| DiOC$_5$(3) | (cationic) | depolarization depends on staining |
| DiOC$_6$(3) |  | concentration and detection method. |
| DiSC$_3$(5) |  |  |
| DiIC$_1$(5) |  |  |
| JC-1 | Carbocyanine | Slow; fluorescence emission ratio |
| JC-9 | (cationic) | 585/520 nm increases upon membrane hyperpolarization. |
| Tetramethyl-rhodamine methyl and ethyl esters Rhodamine 123 | Rhodamine (cationic) | Slow; used to obtain unbiased images of potential-dependent dye distribution. |
| Oxonol V | Oxonol | Slow; fluorescence decreases upon |
| Oxonol VI | (anionic) | membrane hyperpolarization. |
| DiBAC$_4$(3) | Oxonol | Slow; fluorescence decreases |
| DiBAC$_4$(5) | (anionic) | upon membrane hyperpolarization. |
| DiSBAC$_2$(3) |  |  |
| Merocyanine 540 | Merocyanine | Fast/Slow (biphasic response). |

Indo- (DiI), thia- (DiS) and oxa- (DiO) carbocyanines with short alkyl tails (<7 carbon atoms) were among the first potentiometric fluorescent probes developed. These cationic dyes accumulate on hyperpolarized membranes and are translocated into the lipid bilayer. DiOC$_6$(3) (3,3'-dihexyloxacarbocyanine iodide), a cell-permeant, voltage sensitive, green-fluorescent dye, has been the most widely used carbocyanine dye for membrane potential measurements, followed closely by DiOC$_5$(3) (3,3'-dipentyloxacarbocyanine iodide). Thus, in a preferred embodiment of the methods according to the present invention, membrane potentials may be measured using $DiOC_6(3)$ in conjunction with a fluorescence spectrometer.

In one embodiment, the cells are incubated in the presence of $K^+$. In another embodiment, the cells are incubated in the absence of $K^+$. As used herein, "presence of $K^+$" preferably means a $K^+$ concentration in the range of approximately 2 mM to 7 mM, preferably approximately 5 mM.

The present methods may be used with any cell type, such as, but not limited to, erythrocytes, platelets, leukocytes, macrophages, monocytes, dendritic cells, fibroblasts, epidermal cells, mucosal tissue cells, cells in the cerebrospinal fluid, and hair cells. Cells present in blood, skin cells, hair cells, or mucosal tissue cells may be more convenient to use because of the ease of harvesting these cell types.

The methods described in the present application can be used to prevent stimulant abuse, verify patient response to prescribed stimulant, adjust dosage and verify clinical diagnosis.

Bipolar Disorder drugs that may be used in the methods of the present invention include, but are not limited to: 1) mood Stabilizers such as Lithium, Cibalith, Eskalith, Lithane, Litho-tabs, Lithobid; 2) Anti-psychotics such as Abilify, Geodon, Haldol, Risperdol, Saphris, Seroquel, Zyprexa, Symbyax; 3) Anti-anxiety Drugs such as Ativan, Klonopin, Valium, Xanax; 4) Anti-convulsants such as Depakote, Lamictal, Tegretol.

ADHD drugs that may be used according to the methods of the present invention include, but are not limited to, stimulants such as Aderall, Concerta, Desoxysyn, Dexadrine, Focalin, Metadate, Methylin, Ritalin, Vyvanse and non-stimulants such as Intuniv and Strattera.

EXAMPLES

The following examples demonstrate some exemplary uses of the present invention. These examples are provided for illustrative purposes only and are in no way intended to limit the scope of the invention.

Certain patients from the outpatient private psychiatric practice were retested after widely varying intervals as shown in the following Examples. Participation was completely voluntary and only allowed after the signing of a consent form. For the purpose of maintaining the privacy of the subject the lab work was performed confidentially (called blinding of the tester). Each patient was assigned an identification (ID) number and only the clinician had access to the key which correlated ID numbers with patient names. Because these were and are patients presenting for treatment, the priority has been their treatment. They have manifested all the typical variability found in clinical practice, and the resulting data points obtained are those possible under these circumstances. The paired MPR™ results are presented along with clinical vignettes. The patients with repeated tests are shown in example 1 and their vignettes are elucidated here. This clinical data and its interpretation provide the basis for the claims of the invention.

Example 1

MPR™ Returns to ADHD Range after Cessation of Stimulants

A 29 year old female subject was part initially evaluated. See "A" in FIG. 1. At the time the blood was drawn, the subject was taking only mixed amphetamine salts and was symptomatic with longstanding depression, and was not overly responsive to various categories of psychotropics tried previously. On the contemporaneous WHO screener, the subject scored positive on 3 of the 6 items. During the evaluation process the subject indicated that she was not sure she had ADHD but thought that the mixed amphetamine salts she had been taking for some time helped her with her Obsessive-Compulsive Disorder (OCD) symptoms.

A trial of adding mirtazapine was unsuccessful, and in the process of titrating off of mirtazapine as a preliminary to her trying a selegiline patch, she also stopped taking mixed amphetamine salts. Two weeks after stopping the mixed amphetamine salts, she scored positive on 4 of the 6 items on the WHO screener, indicative of ADHD. Her blood was drawn the third week after stopping mixed amphetamine salts. That MPR™ value returned to the ADHD range as shown in FIG. 1. See "B" in FIG. 1. The concordance of the MPR™ result and the subject's self-report of sufficiently severe symptomatology on the WHO screener pointed to the consideration of ADHD as a valid diagnosis. Subsequent review of DSM-IV-TR™ criteria suggested a diagnosis of ADHD in which the subject endorsed four, but not six, of the criteria for inattention. On selegiline transdermal 12 mg per 24 hours and mixed amphetamine salts 15 mg per day, the subject scored 1 out of the six items on the WHO screener. This positive result was taken as validation of the diagnosis of Comorbid ADHD. This vignette illustrates that for this subject, the MPR™ fairly quickly returns to the ADHD range from the negative (normal) range after stopping relevant treatment, and was concordant with an increase in symptomatology.

Example 2

MPR™ Alerts to Comorbid ADHD and Returns to Negative Range after Treatment

A 31 year old male tested positive for ADHD. See "A" in FIG. 2. At that time, the subject was clinically diagnosed with BD and was responding well to lithium therapy. The subject was also taking methadone 120 mg per day. Contemporaneously, the subject scored positive on 4 of the 6 items on the WHO screener. The subject also scored positive on two of the areas on Barkley's Quick-Check for Adult ADHD Diagnosis. The subject scored negative on the Recall of Childhood Behavior section on the Barkley Rating Scale even with his Mom's input. The subject was diagnosed with comorbid ADHD despite the sketchy recall of his childhood symptoms. Treatment was started at that time and the subject was compliant on mixed amphetamine salts 40 mg every morning, which offered good symptomatic control and left him positive on only two out of the six items on the WHO screener. At that time, the subject was taking lamotrigine instead of lithium for treatment of BD. He was assigned a new ID #B 11-157 and tested again. That MPR™ test result was in the negative range as shown in "B" in FIG. 2. This return to the normal range is concordant with the subject's clinically significant reduction in symptoms referable to ADHD. Additionally the subject was feeling clinically stable enough on mixed amphetamine salts in addition to his pharmacological treatment for BD that he resumed downward titration of his methadone.

This patient had to be switched to dextroamphetamine sulfate 5 mg three times per day and extended release dexmethylphenidate 20 mg each morning, which was then increased to one in the morning and one in the afternoon because the benefit was wearing off. During the appointment, the subject indicated that his pharmacist informed him that a mixed amphetamine salt in a 20 mg dosage was again available, and he was interested in getting a prescription so that he could resume the 40 mg per day dose on which he had done well for so long. At that appointment, a blood sample was taken, ID #B 11-232, which tested in the ADHD transition range (see "C" in FIG. 2), correlating with his report of the dextroamphetamine's and extended release dexmethylphenidate's not working as well for him in terms of clinical benefit. That combination did not return his membrane potential as measured back to the normal range as had 40 mg of mixed amphetamine salts each day, which he wanted to return to taking because subjectively he knew that that was what had worked better for him.

Example 3

In BD Patient MPR™ Returns to Negative with Treatment

A 43 year old woman with a long standing diagnosis of BD and comorbid difficulties with alcohol from well before the start of her treatment. At the time of the subject's first blood draw, she reported being off of her medications for BD for one month, without clinical symptoms, and tested in the BD range (See "A" in FIG. 3). When retested, the subject was taking lithium, quetiapine, and mirtazapine for some time, and was back at work. The result obtained was in the negative (normal) range (See "B" in FIG. 3) when she was reasonably stable and taking medication appropriate for her diagnosis.

Subsequently, the subject reported anxiety, occurring while she continued taking lithium, quetiapine, and mirtazapine. The subject thought she was experiencing a return of bipolar symptomatology, but it was discussed that this could be situational instead; namely, due to the subject's awareness of issues with her fiancé and impending wedding. This awareness was "bolstered" by the notion that the subject's MPR™ test had been in the normal range on her medication regimen not so many months before. Time limited couples therapy was suggested, and the subject was given very low dosage perphenazine for neurotic anxiety. The perphenazine was quickly discontinued by the subject because of blurred vision. the subject's issues with her fiancé resolved and she continued on lithium, quetiapine, and mirtazapine. The result in the negative range helped in the decision to essentially stay the course with the medications associated with that result.

Example 4

Example of BD Transition to ADHD

A 32 year old woman initially evaluated by a psychiatrist, and not fully stabilized on aripiperazole, citalopram, oxcarbazepine, and alprazolam for her diagnosis of Bipolar I Disorder. The first MPR™ test, when the subject was tapering from oxcarbazepine, and taking escitalopram 10 mg per day, aripiperazole 2 mg per day, and alprazolam 0.5 mg twice a day as needed, was in the bipolar transition range (see "A" in FIG. 4). This was compatible with partially treated Bipolar Disorder. Subsequently, the subject's mood was further stabilized clinically with the addition of lithium 600 mg per day, Seroquel 100 mg at bedtime, and when retested, tested in the ADHD range (see "B" in FIG. 4). At that time, the subject was self-rated as being positive on 5 out of 6 items on the WHO screener, and 12 out of 18 total items. This led to a discussion of the presence of any childhood symptoms. The subject endorsed some childhood symptoms of ADHD, but there was no history obtained of diagnosis or treatment of those symptoms in childhood. Additionally, the subject met the DSM IV criteria for ADHD, combined type, 314.01, and was started on methylphenidate 10 mg twice per day and later increased to 10 mg three times per day. The subject reported benefit with the addition of methylphenidate including being able to sit through a movie, decreased anxiety and impulsivity and irritability and that "my desk is clean" attitude. Also, the subject decreased her alprazolam to 0.25 mg twice per day as needed.

Example 5

MPR™ Alerting to the Potential Presence of Comorbid ADHD

A 33 year old woman presented with a complaint of depression starting at the age eleven with symptoms of depression continuing off and on over the years. At the time of her evaluation, the subject was significantly depressed, self-rated 3 on a scale of 10, with thoughts of helplessness and hopelessness and self-harm. At that time, the subject's concentration was "a little worse." At the time of that evaluation the subject was already on sertraline 100 mg at bedtime, which was no longer working according to the subject. She reported symptoms of panic attacks, but other SSRI's by history had not offered a benefit, nor bupropion. There was a family history of suicide in her mother's siblings. The subject was sufficiently impaired that she was placed off work. There was no history of hypomanic or manic symptoms elicited. Despite no history of hospitalization, the initial diagnosis was Major Depression, recurrent, and duloxetine 30 mg per day was added. The subject was told that an early onset of depression often pointed to a diagnosis of bipolarity and to watch for any symptoms of feeling too good too quickly with the duloxetine.

At the time of the initial evaluation, a blood sample was drawn. The MPR™ result was in the BD transition range (see "A" in FIG. 5). The subject was told to discontinue the duloxetine out of concern that the duloxetine could potentially induce hypomania. The diagnosis was then later changed to cyclothymia, possibly an under diagnosis, and started on lamotrigine, to be tapered up as per a starter pack. This offered benefit quickly and the subject was able to return to work. The lamotrigine was steadily increased and the subject steadily reported further benefit with it. The regimen on which the subject continued was sertraline 50 mg per day and lamotrigine 200 mg per day and benefit continues without complaint of side effects. She was retested (blood sample ID #B 11-203) in the ADHD range (see "B" in FIG. 5). On the WHO screener, the subject scored 0 on the 6 screening items and only 1 out of the total possible of 18. She was doing well clinically and no adjustment was made in her medication regimen. It is possible that the lamotrigine decreased the subject's neuronal excitability and membrane potential a little too much, but again she is doing well clinically and no further adjustment was made. The overall sense of the clinician was that with the early indication of the potential for bipolarity, an optimal clinical result was obtained. When the subject was later retested, she showed progress and her medications were slightly to extended release methylphenidate 36 mg each morning and double the immediate release methylphenidate, 10 mg twice per day along with bupropion, 200 mg extended release twice per day, with the lamotrigine unchanged at 150 mg twice per day. This case was consistent with others with the MPR™ detecting the potential presence of comorbid ADHD or ADD.

Example 6

MPR™ Test Adjusted Overcorrection for ADHD Treatment

A 64 year old patient was first diagnosed with ADHD as shown in FIG. 6, and prescribed 10 mg of methylphenidate. The subject was later retested, and the MPR™ value was close to the BD side of the negative range. The patient was prescribed 5 mg of methylphenidate and tested again at a later date. The MPR™ value moved up close to the right value. In this example, the MPR™ test was used to titrate the medication levels for the appropriate treatment.

Implications of the Results in the Examples for Clinical Practice

Getting the MPR test result positively affected treatment outcomes for the patients described above in the Examples. First, the question of whether each had BD, an important question that significantly affects treatment options and subsequent medication risks, was answered. The test provided information supporting the diagnosis of ADHD in both patients where BD was a reasonable consideration. This is important because there is symptom overlap between the diagnoses of ADHD and BD which can add to the diagnostic uncertainty. Also, without a biologic marker for disease, psychiatric patients are commonly subjected to trials of medication based on the best evidence-based algorithms available and the clinical expertise of the person treating the patient. For instance, especially when the diagnosis of BD is not clear, even with the best clinical expertise, it can sometimes take years to establish a correct diagnosis and initiate the appropriate treatment. Unrecognized ADHD in both children and adults can cause a lifetime of under-achievement and overlying anxiety and depression. Particularly in the case of adults, the depression and anxiety are recognized and treated but the underlying ADHD can go unrecognized contributing to problems in all areas of life. Untreated ADHD in adulthood affects relationships, jobs, household and financial management, especially as adult responsibilities grow, leaving a mark on a person's self-esteem. As the MPR™ test provides the additional information of a biologic marker, the amount of time, money, and unnecessary medication trials for BD, with their associated side effects can be minimized or avoided. Such was the case for the patients described above.

Second, the definitive test result indicating a diagnosis of ADHD gave the patients more incentive to accept the diagnosis of ADHD. Their greater understanding of ADHD and recognizing how it manifests for them has helped them to better manage their symptoms. As treatment of ADHD requires that the patient learn strategies to manage their symptoms, and not just taking medication, this greater understanding has been invaluable.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method of optimizing a drug therapy treatment for a human patient with attention-deficit/hyperactivity disorder (ADHD), comprising:

obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug therapy for ADHD;

comparing the ratio to (a) and/or (b):

(a) a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$, (b) an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$;

wherein each mean membrane potential is determined by incubating the cells in vitro in buffer comprising a potential-sensitive dye, resuspending the cells in potential-sensitive dye free-buffer, and measuring cell fluorescence; and identifying an optimal effective drug therapy for treatment of the human patient with ADHD when the ratio obtained is not significantly different from the control ratio in (a) and/or is significantly higher than the ADHD control ratio in (b);

adjusting the drug therapy for ADHD to the optimal effective drug therapy identified; and administering the optimal effective drug therapy to the human patient with ADHD.

2. A method of optimizing a drug treatment therapy for a human patient with bipolar disorder (BD), comprising:

obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug therapy for BD;

comparing the ratio to (a) and/or (b):
(a) a control ratio of a mean membrane potential of control human cells known to not have BD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$,
(b) a BD control ratio of a mean membrane potential of BD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$;

wherein each mean membrane potential is determined by incubating the cells in vitro in buffer comprising a potential-sensitive dye, resuspending the cells in potential-sensitive dye free-buffer, and measuring cell fluorescence; and identifying an optimal effective drug therapy for treatment of the human patient with BD when the ratio obtained is not significantly different from the control ratio in (a) and/or is significantly lower than the BD control ratio in (b);

adjusting the drug therapy for BD to the optimal effective drug therapy identified; and administering the optimal effective drug therapy to the human patient with BD.

3. A method of optimizing a drug therapy treatment for a human patient with attention-deficit/hyperactivity disorder (ADHD), comprising the steps of:

performing a drug therapy treatment for the patient with ADHD with at least one drug;

obtaining at least one sample from the patient with ADHD which is collected after the drug therapy treatment with at least one drug;

performing on each sample, a mean membrane potential test comprising:
obtaining a ratio of a mean membrane potential from a first population of cells from the sample incubated in vitro in the presence of a compound that alters $Na^+K^+$ ATPase activity and in the absence of $K^+$, to a mean membrane potential from a second population of cells from the sample incubated in vitro in the absence of the compound that alters $Na^+K^+$ ATPase activity and in the presence or absence of $K^+$, comparing the ratio of the mean membrane potential to (a) and/or (b):
(a) a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$,
(b) an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$;

modifying at least one drug in the drug therapy treatment based on the mean membrane potential test;

identifying an optimal effective drug therapy treatment for the human patient with ADHD when the ratio of the mean membrane potential obtained is not significantly different from the control ratio in (a) and/or is significantly higher than the ADHD control ratio in (b); and administering the optimal effective drug therapy treatment to the human patient with ADHD.

4. A method of optimizing a drug therapy treatment for a human patient with bipolar disorder (BD), comprising the steps of:

performing a drug therapy treatment for the patient with BD with at least one drug;

obtaining at least one sample from the patient with BD which is collected after the drug therapy treatment with at least one drug;

performing on each sample, a mean membrane potential test comprising:
obtaining a ratio of a mean membrane potential from a first population of cells from the sample incubated in vitro in the presence of a compound that alters $Na^+K^+$ ATPase activity and in the absence of $K^+$, to a mean membrane potential from a second population of cells from the sample incubated in vitro in the absence of the compound that alters $Na^+K^+$ ATPase activity and in the presence or absence of $K^+$, comparing the ratio of the mean membrane potential to (a) and/or (b):
(a) a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$,
(b) a BD control ratio of a mean membrane potential of BD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$;

modifying at least one drug in the drug therapy treatment based on the mean membrane potential test;

identifying an optimal effective drug therapy treatment for the human patient with BD when the ratio of the mean membrane potential obtained is not significantly different from the control ratio in (a) and/or is significantly lower than the BD control ratio in (b); and administering the optimal effective drug therapy treatment to the human patient with BD.

5. The method according to claim 1, 2, 3, or 4, further comprising obtaining an initial ratio of a mean membrane potential from an initial population of cells from the human patient before the obtaining step or the performing the drug therapy treatment step.

6. The method according to claim 1, 2, 3, or 4, wherein steps (a) and (b) are performed.

7. The method according to claim 1, 2, 3, or 4, wherein $K^+$ is present at a concentration of 2-7 mM.

8. The method according to claim 1, 2, 3, or 4, wherein the compound that alters $Na^+K^+$ ATPase activity is selected from the group consisting of: valinomycin, monensin, monensin decyl ester, p-chloromercurybenzenesulfonate (PCMBS), veratridine, ethacrynate, dopamine, a catecholamine, a phorbol ester, ouabain, lithium, valproate, lamotrigine, cocaine, nicotine, R0-31-8220, oxymetazoline, calcineurin, topiramate, a peptide hormone, sorbitol, and a diuretic.

9. The method according to claim 1, 2, 3, or 4, wherein the compound that alters $Na^+K^+$ ATPase activity is a phorbol ester.

10. The method according to claim 9, wherein the phorbol ester is selected from the group consisting of: phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate.

11. The method according to claim 1, 2, 3, or 4, wherein each of the cells used therein is selected from the group consisting of lymphoblasts, erythrocytes, platelets, leukocytes, macrophages, monocytes, dendritic cells, fibroblasts, epidermal cells, mucosal tissue cells, cells of cerebrospinal fluid, hair cells, and cells of whole blood.

12. A method of optimizing a drug dosage for treatment of a human patient with attention-deficit/hyperactivity disorder (ADHD), comprising:
obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug dosage for ADHD;
comparing the ratio to (a) and/or (b):
(a) a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$,
(b) an ADHD control ratio of a mean membrane potential of ADHD control human cells known to have ADHD incubated in vitro in the presence of the compound that alters $Na^+K^+$ ATPase activity and in the absence of $K^+$, to a mean membrane potential of the ADHD control human cells incubated in vitro in the presence of the compound that alters $Na^+K^+$ ATPase activity and in the presence or absence of $K^+$;
wherein each mean membrane potential is determined by incubating the cells in vitro in buffer comprising a potential-sensitive dye, resuspending the cells in potential-sensitive dye free-buffer, and measuring cell fluorescence;
identifying an optimal drug dosage effective for treatment of the human patient with ADHD when the ratio obtained is not significantly different from the control ratio in (a) and/or is significantly higher than the ADHD control ratio in (b);
adjusting the drug therapy treatment of the human patient with ADHD to the optimal effective drug dosage identified; and
administering the optimal effective drug dosage to the human patient with ADHD.

13. A method of optimizing a drug dosage for treatment of a human patient with bipolar disorder (BD), comprising:
obtaining a ratio of a mean membrane potential from a first population of cells from the human patient incubated in vitro in the presence of a compound that alters $Na^+K^+$ ATPase activity and in the absence of $K^+$, to a mean membrane potential from a second population of cells from the human patient incubated in vitro in the absence of the compound that alters $Na^+K^+$ ATPase activity and in the presence or absence of $K^+$, following treatment of the human patient with a drug dosage for ADHD;
comparing the ratio to (a) and/or (b):
(a) a control ratio of a mean membrane potential of control human cells known to not have ADHD incubated in vitro in the presence of the compound that alters $Na^+K^+$ ATPase activity and in the absence of $K^+$, to a mean membrane potential of the control human cells incubated in vitro in the absence of the compound that alters $Na^+K^+$ ATPase activity and in the presence or absence of $K^+$,
(b) a BD control ratio of a mean membrane potential of BD control human cells known to have BD incubated in vitro in the presence of the compound that alters $Na^+K^+$ ATPase activity and in the absence of $K^+$, to a mean membrane potential of the BD control human cells incubated in vitro in the presence of the compound that alters $Na^+K^+$ ATPase activity and in the presence or absence of $K^+$;
wherein each mean membrane potential is determined by incubating the cells in vitro in buffer comprising a potential-sensitive dye, resuspending the cells in potential-sensitive dye free-buffer, and measuring cell fluorescence; and
identifying an optimal drug dosage effective for treatment of the human patient with BD when the ratio obtained is not significantly different from the control ratio in (a) and/or is significantly lower than the BD control ratio in (b);
adjusting the drug therapy treatment of the human patient with BD to the optimal effective drug dosage identified; and
administering the optimal effective drug dosage to the human patient with BD.

14. A method of optimizing a drug dosage for treatment of a human patient with attention-deficit/hyperactivity disorder (ADHD), comprising the steps of:
treating the human patient with a dosage of a drug for ADHD;
obtaining at least one sample from the human patient which is collected after the treating step;

performing on each sample, a mean membrane potential test comprising:
    obtaining a ratio of a mean membrane potential from a first population of cells from the sample incubated in vitro in the presence of a compound that alters Na$^+$K$^+$ ATPase activity and in the absence of K$^+$, to a mean membrane potential from a second population of cells from the sample incubated in vitro in the absence of the compound that alters Na$^+$K$^+$ ATPase activity and in the presence or absence of K$^+$,
    comparing the ratio of the mean membrane potential to (a) and/or (b):
        (a) a control ratio of a mean membrane potential of control human cells known to not have ADHD incubated in vitro in the presence of the compound that alters Na$^+$K$^+$ ATPase activity and in the absence of K$^+$, to a mean membrane potential of the control human cells incubated in vitro in the absence of the compound that alters Na$^+$K$^+$ ATPase activity and in the presence or absence of K$^+$,
        (b) an ADHD control ratio of a mean membrane potential of ADHD control human cells known to have ADHD incubated in vitro in the presence of the compound that alters Na$^+$K$^+$ ATPase activity and in the absence of K$^+$, to a mean membrane potential of the ADHD control human cells incubated in vitro in the presence of the compound that alters Na$^+$K$^+$ ATPase activity and in the presence or absence of K$^+$;
    modifying the drug dosage based on the mean membrane potential test;
    identifying an optimal effective drug dosage for treating the human patient with ADHD when the ratio of the mean membrane potential obtained is not significantly different from the control ratio in (a) and/or is significantly higher than the ADHD control ratio in (b); and
    administering the optimal effective drug dosage to the human patient with ADHD.

15. A method of optimizing a drug dosage for treatment of a human patient bipolar disorder (BD), comprising the steps of:
    treating the human patient with a dosage of a drug for BD;
    obtaining at least one sample from the human patient which is collected after the treating step;
    performing on each sample, a mean membrane potential test comprising:
        obtaining a ratio of a mean membrane potential from a first population of cells from the sample incubated in vitro in the presence of a compound that alters Na$^+$K$^+$ ATPase activity and in the absence of K$^+$, to a mean membrane potential from a second population of cells from the sample incubated in vitro in the absence of the compound that alters Na$^+$K$^+$ ATPase activity and in the presence or absence of K$^+$,
        comparing the ratio of the mean membrane potential to (a) and/or (b):
            (a) a control ratio of a mean membrane potential of control human cells known to not have ADHD incubated in vitro in the presence of the compound that alters Na$^+$K$^+$ ATPase activity and in the absence of K$^+$, to a mean membrane potential of the control human cells incubated in vitro in the absence of the compound that alters Na$^+$K$^+$ ATPase activity and in the presence or absence of K$^+$,
            (b) a BD control ratio of a mean membrane potential of BD control human cells known to have BD incubated in vitro in the presence of the compound that alters Na$^+$K$^+$ ATPase activity and in the absence of K$^+$, to a mean membrane potential of the BD control human cells incubated in vitro in the presence of the compound that alters Na$^+$K$^+$ ATPase activity and in the presence or absence of K$^+$;
    modifying the drug dosage based on the mean membrane potential test;
    identifying an optimal effective drug dosage for treating the human patient with BD when the ratio of the mean membrane potential obtained is not significantly different from the control ratio in (a) and/or is significantly lower than the BD control ratio in (b); and
    administering the optimal effective drug dosage to the human patient with BD.

16. The method according to claim 12, 13, 14, or 15, further comprising obtaining an initial ratio of a mean membrane potential from an initial population of cells from the human patient before the treating step or the obtaining step.

17. The method according to claim 12, 13, 14, or 15, wherein steps (a) and (b) are performed.

18. The method according to claim 12, 13, 14, or 15, wherein K$^+$ is present at a concentration of 2-7 mM.

19. The method according to claim 12, 13, 14, or 15, wherein the compound that alters Na$^+$K$^+$ ATPase activity is selected from the group consisting of: valinomycin, monensin, monensin decyl ester, p-chloromercurybenzenesulfonate (PCMBS), veratridine, ethacrynate, dopamine, a catecholamine, a phorbol ester, ouabain, lithium, valproate, lamotrigine, cocaine, nicotine, RO-31-8220, oxymetazoline, calcineurin, topiramate, a peptide hormone, sorbitol, and a diuretic.

20. The method according to claim 12, 13, 14, or 15, wherein the compound that alters Na$^+$K$^+$ ATPase activity is a phorbol ester.

21. The method according to claim 20, wherein the phorbol ester is selected from the group consisting of: phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate.

22. The method according to claim 12, 13, 14, or 15, wherein each of the cells used therein is selected from the group consisting of lymphoblasts, erythrocytes, platelets, leukocytes, macrophages, monocytes, dendritic cells, fibroblasts, epidermal cells, mucosal tissue cells, cells of cerebrospinal fluid, hair cells, and cells of whole blood.

23. A method of treating a human patient with attention-deficit/hyperactivity disorder (ADHD), comprising:
    obtaining a ratio of a mean membrane potential from a first population of cells from the human patient incubated in vitro in the presence of a compound that alters Na$^+$K$^+$ ATPase activity and in the absence of K$^+$, to a mean membrane potential from a second population of cells from the human patient incubated in vitro in the absence of the compound that alters Na$^+$K$^+$ ATPase activity and in the presence or absence of K$^+$, following treatment of the human patient with a drug dosage for ADHD;
    comparing the ratio to (a) and/or (b):
        (a) a control ratio of a mean membrane potential of control human cells known to not have ADHD incubated in vitro in the presence of the compound that alters Na$^+$K$^+$ ATPase activity and in the absence of K$^+$, to a mean membrane potential of the control human cells incubated in vitro in the absence of the compound that alters Na$^+$K$^+$ ATPase activity and in the presence or absence of K$^+$, (b) an ADHD control ratio of a mean membrane potential of ADHD control human cells known to have ADHD incubated in vitro in the presence of the compound that alters Na$^+$K$^+$ ATPase activity and in the absence of K$^+$, to a mean membrane potential of the ADHD control human cells incubated in vitro in the presence of the compound that alters Na$^+$K$^+$ ATPase activity and in the presence or absence of K$^+$;

wherein each mean membrane potential is determined by incubating the cells in vitro in buffer comprising a potential-sensitive dye, resuspending the cells in potential-sensitive dye free-buffer, and measuring cell fluorescence;

adjusting the drug dosage for ADHD to an effective drug dosage for treating the human patient such that the ratio obtained is not significantly different from the control ratio in (a) and/or is significantly higher than the ADHD control ratio in (b); and administering the effective drug dosage to the human patient with ADHD.

24. A method of treating a human patient with bipolar disorder (BD), comprising:

obtaining a ratio of a mean membrane potential from a first population of cells from the human patient incubated in vitro in the presence of a compound that alters Na$^+$K$^+$ ATPase activity and in the absence of K$^+$, to a mean membrane potential from a second population of cells from the human patient incubated in vitro in the absence of the compound that alters Na$^+$K$^+$ ATPase activity and in the presence or absence of K$^+$, following treatment of the human patient with a drug dosage for BD;

comparing the ratio to (a) and/or (b):

(a) a control ratio of a mean membrane potential of control human cells known to not have BD incubated in vitro in the presence of the compound that alters Na$^+$K$^+$ ATPase activity and in the absence of K$^+$, to a mean membrane potential of the control human cells incubated in vitro in the absence of the compound that alters Na$^+$K$^+$ ATPase activity and in the presence or absence of K$^+$, (b) a BD control ratio of a mean membrane potential of BD control human cells known to have BD incubated in vitro in the presence of the compound that alters Na$^+$K$^+$ ATPase activity and in the absence of K$^+$, to a mean membrane potential of the BD control human cells incubated in vitro in the presence of the compound that alters Na$^+$K$^+$ ATPase activity and in the presence or absence of K$^+$;

wherein each mean membrane potential is determined by incubating the cells in vitro in buffer comprising a potential-sensitive dye, resuspending the cells in potential-sensitive dye free-buffer, and measuring cell fluorescence;

adjusting the drug dosage for BD to an effective drug dosage for treating the human patient such that the ratio obtained is not significantly different from the control ratio in (a) and/or is significantly lower than the BD control ratio in (b); and administering the effective drug dosage to the human patient with BD.

25. A method of treating a human patient with attention-deficit/hyperactivity disorder (ADHD), comprising the steps of:

treating the human patient with a dosage of a drug for ADHD;

obtaining at least one sample from the human patient which is collected after the treating step;

performing on each sample, a mean membrane potential test comprising:

obtaining a ratio of a mean membrane potential from a first population of cells from the sample incubated in vitro in the presence of a compound that alters Na$^+$K$^+$ ATPase activity and in the absence of K$^+$, to a mean membrane potential from a second population of cells from the sample incubated in vitro in the absence of the compound that alters Na$^+$K$^+$ ATPase activity and in the presence or absence of K$^+$, comparing the ratio of the mean membrane potential to (a) and/or (b):

(a) a control ratio of a mean membrane potential of control human cells known to not have ADHD incubated in vitro in the presence of the compound that alters Na$^+$K$^+$ ATPase activity and in the absence of K$^+$, to a mean membrane potential of the control human cells incubated in vitro in the absence of the compound that alters Na$^+$K$^+$ ATPase activity and in the presence or absence of K$^+$, (b) an ADHD control ratio of a mean membrane potential of ADHD control human cells known to have ADHD incubated in vitro in the presence of the compound that alters Na$^+$K$^+$ ATPase activity and in the absence of K$^+$, to a mean membrane potential of the ADHD control human cells incubated in vitro in the presence of the compound that alters Na$^+$K$^+$ ATPase activity and in the presence or absence of K$^+$;

adjusting the drug dosage for ADHD to an effective drug dosage for treating the human patient such that ratio of the mean membrane potential obtained is not significantly different from the control ratio in (a) and/or is significantly higher than the ADHD control ratio in (b); and administering the effective drug dosage to the human patient with ADHD.

26. A method of treating a human patient with bipolar disorder (BD), comprising the steps of:

treating the human patient with a dosage of a drug for BD;

obtaining at least one sample from the human patient which is collected after the treating step;

performing on each cell sample, a mean membrane potential test comprising:

obtaining a ratio of a mean membrane potential from a first population of cells from the cell sample incubated in vitro in the presence of a compound that alters Na$^+$K$^+$ ATPase activity and in the absence of K$^+$, to a mean membrane potential from a second population of cells from the cell sample incubated in vitro in the absence of the compound that alters Na$^+$K$^+$ ATPase activity and in the presence or absence of K$^+$, comparing the ratio of the mean membrane potential to (a) and/or (b):

(a) a control ratio of a mean membrane potential of control human cells known to not have ADHD incubated in vitro in the presence of the compound that alters Na⁺K⁺ ATPase activity and in the absence of K⁺, to a mean membrane potential of the control human cells incubated in vitro in the absence of the compound that alters Na⁺K⁺ ATPase activity and in the presence or absence of K⁺, (b) a BD control ratio of a mean membrane potential of ADHD control human cells known to have BD incubated in vitro in the presence of the compound that alters Na⁺K⁺ ATPase activity and in the absence of K⁺, to a mean membrane potential of the BD control human cells incubated in vitro in the presence of the compound that alters Na⁺K⁺ ATPase activity and in the presence or absence of K⁺;

adjusting the drug dosage for BD to an effective drug dosage for treating the human patient such that ratio of the mean membrane potential obtained is not significantly different from the control ratio in (a) and/or is significantly lower than the BD control ratio in (b); and administering the effective drug dosage to the human patient with BD.

27. The method according to claim 23, 24, 25 or 26, further comprising obtaining an initial ratio of a mean membrane potential from an initial population of cells from the human patient before the treating step or obtaining step.

28. The method according to claim 23, 24, 25, or 26, wherein steps (a) and (b) are performed.

29. The method according to claim 23, 24, 25, or 26, wherein K⁺ is present at a concentration of 2-7 mM.

30. The method according to claim 23, 24, 25, or 26, wherein the compound that alters Na⁺K⁺ ATPase activity is selected from the group consisting of: valinomycin, monensin, monensin decyl ester, p-chloromercurybenzenesulfonate (PCMBS), veratridine, ethacrynate, dopamine, a catecholamine, a phorbol ester, ouabain, lithium, valproate, lamotrigine, cocaine, nicotine, R0-31-8220, oxymetazoline, calcineurin, topiramate, a peptide hormone, sorbitol, and a diuretic.

31. The method according to claim 23, 24, 25, or 26, wherein the compound that alters Na⁺K⁺ ATPase activity is a phorbol ester.

32. The method according to claim 31, wherein the phorbol ester is selected from the group consisting of: phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate.

33. The method according to claim 23, 24, 25, or 26, wherein each of the cells used therein is selected from the group consisting of lymphoblasts, erythrocytes, platelets, leukocytes, macrophages, monocytes, dendritic cells, fibroblasts, epidermal cells, mucosal tissue cells, cells of cerebrospinal fluid, hair cells, and cells of whole blood.

* * * * *